United States Patent [19]

Nakayama et al.

[11] Patent Number: 4,521,190
[45] Date of Patent: Jun. 4, 1985

[54] AIR BEARING DEVICE IN DENTAL HANDPIECE

[75] Inventors: Shozo Nakayama; Sekiya Ogino, both of Kyoto, Japan

[73] Assignee: Kabushiki Kaisha Morita Seisakusho, Kyoto, Japan

[21] Appl. No.: 517,948

[22] Filed: Jul. 27, 1983

[30] Foreign Application Priority Data

Jul. 28, 1982 [JP] Japan ................................ 57-132895

[51] Int. Cl.³ .............................................. A61C 1/05
[52] U.S. Cl. ...................................... 433/132; 384/112
[58] Field of Search ......................... 433/132; 384/112

[56] References Cited

U.S. PATENT DOCUMENTS 3,837,716 9/1974 Allen et al. ........................ 384/112
4,326,846 4/1982 Sugai et al. ........................ 433/132

Primary Examiner—John J. Wilson
Attorney, Agent, or Firm—Koda and Androlia

[57] ABSTRACT

An improvement in an air bearing device of an air drive, air journal type dental handpiece is disclosed, wherein a radial gap for journaling a rotor in the radial direction comprises partially enlarged gaps which, serving as air pools, improve the handpiece's cutting performance and prevent abnormal noise and vibration of the turbine blade caused by the whirl phenomenon.

3 Claims, 8 Drawing Figures

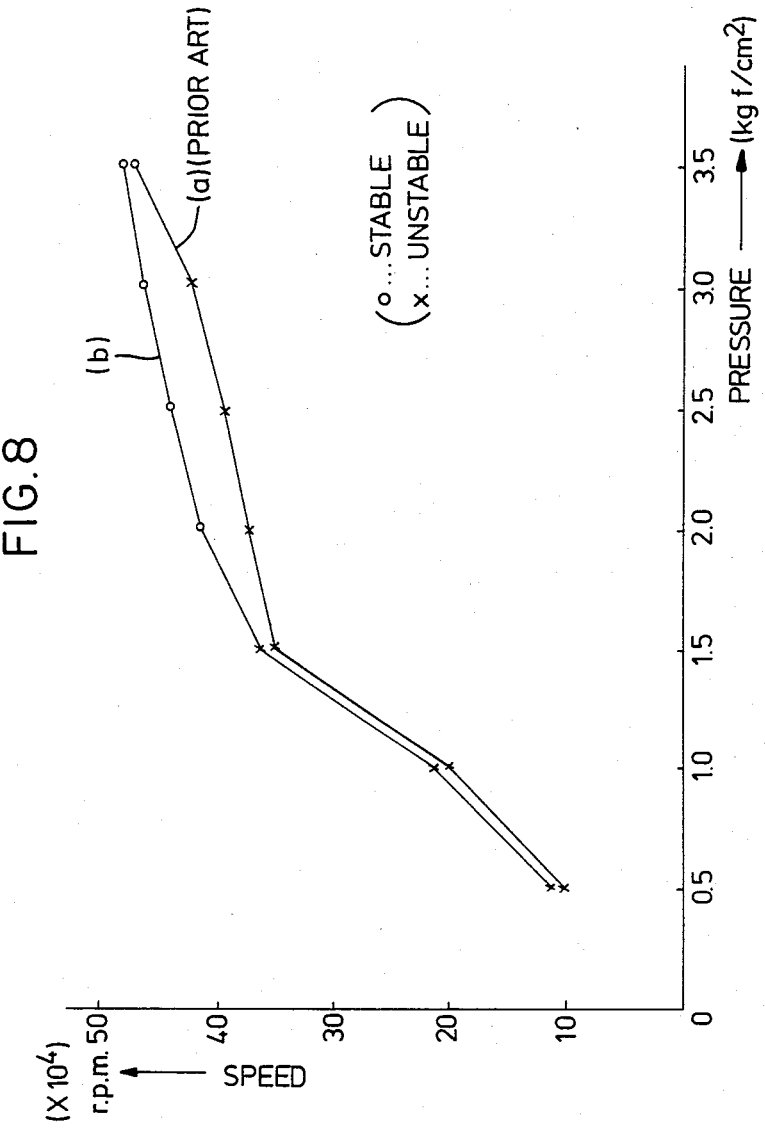

AIR BEARING DEVICE IN DENTAL HANDPIECE

BACKGROUND OF THE INVENTION

1. Field of the Invention

The present invention relates to an air bearing and more particularly to an air bearing device for a dental handpiece.

2. Prior Art

The structure of an existing air journal type handpiece has several problems.

As seen from FIG. 1, a front sectional view, a turbine rotor 2 holding a cutting tool shaft 1 is positioned in a bearing so as to form therebetween a radial gap 3 and thrust gaps 4. High velocity compressed fluid (compressed air) is fed into these gaps 3 and 4 through air channels 6, inlet holes 7, and bearing orifices 8. The orifices 8 form a thin air-film in the gaps 3 and 4 for the rotating rotor 2 (at 500,000 r.p.m.max.) to be journaled radially as well as thrustwise. In the figure, there are also shown an exhaust channel 9, turbine blades 10, elastic —O—rings 11, air channel 12 for driving the turbine blades 10, handpiece casing 13, and an end cap 14. In the prior art the bearing 5 includes the surface of a rotatable body that has a tool shaft 1 as its axis such as a hollow cylinder or the like or a truncated cone. However, with the combination of such a rotatble body and a rotor 2, there is a limit to the load capacity or bearing stiffness. The small bearing stiffness causes a so-called whirl phenomenon, and the small load capacity causes contact noise between the bearing 5 and the rotor 2 to aggravate the clinic enviornment. In addition, the design damages the confronting faces of the rotor 2 and the bearing 5, resulting in poor durability. Furthermore, it is noted among others that the rotor speed decreases as much as 1,000,000 r.p.m. due to the whirl phenomenon compared with when the cutting tool shaft 1 is not set in the rotor.

The present inventors secured earlier two patents that solve the problems in the prior art: U.S. Pat. Nos. 4,326,846 and 4,209,293. The former patent relates to an invention in which each of the turbine blades is provided with a partially communicating channel, and the part of the air guided by the channel drives the turbine blade in its rotational direction to improve the torque efficiency. The latter patent is for an invention in which throttling parts are provided in the thrust end face of the air bearing in order to substantially increase the centripetal thrust gap to improve the bearing stiffness, and the throttling parts defines an air pool.

SUMMARY OF THE INVENTION

Therefore, it is a primary object of the present invention to provide an improved bearing device wherein the radial gap is provided with a multiplicity of partial air pools along the periphery of the radial gap with simultaneous arrangement not to interfere with the longitudinal airflow of the radial gap because of the air bearing. The air pools are formed by recesses which are spacedly formed in the rotor or the opposite face of the bearing.

In the accompanying drawings, there are shown illustrative embodiments of the invention from which these and other objects, novel features, and advantages of the invention will be readily apparent.

BRIEF DESCRIPTION OF THE DRAWINGS

FIG. 8 is a comparative graph showing the relationship between pressure and revolutional speed and stability of a handpiece provided with the device of the present invention and a prior art counterpart.

DETAILED EXPLANATION OF THE INVENTION

Figure 1:
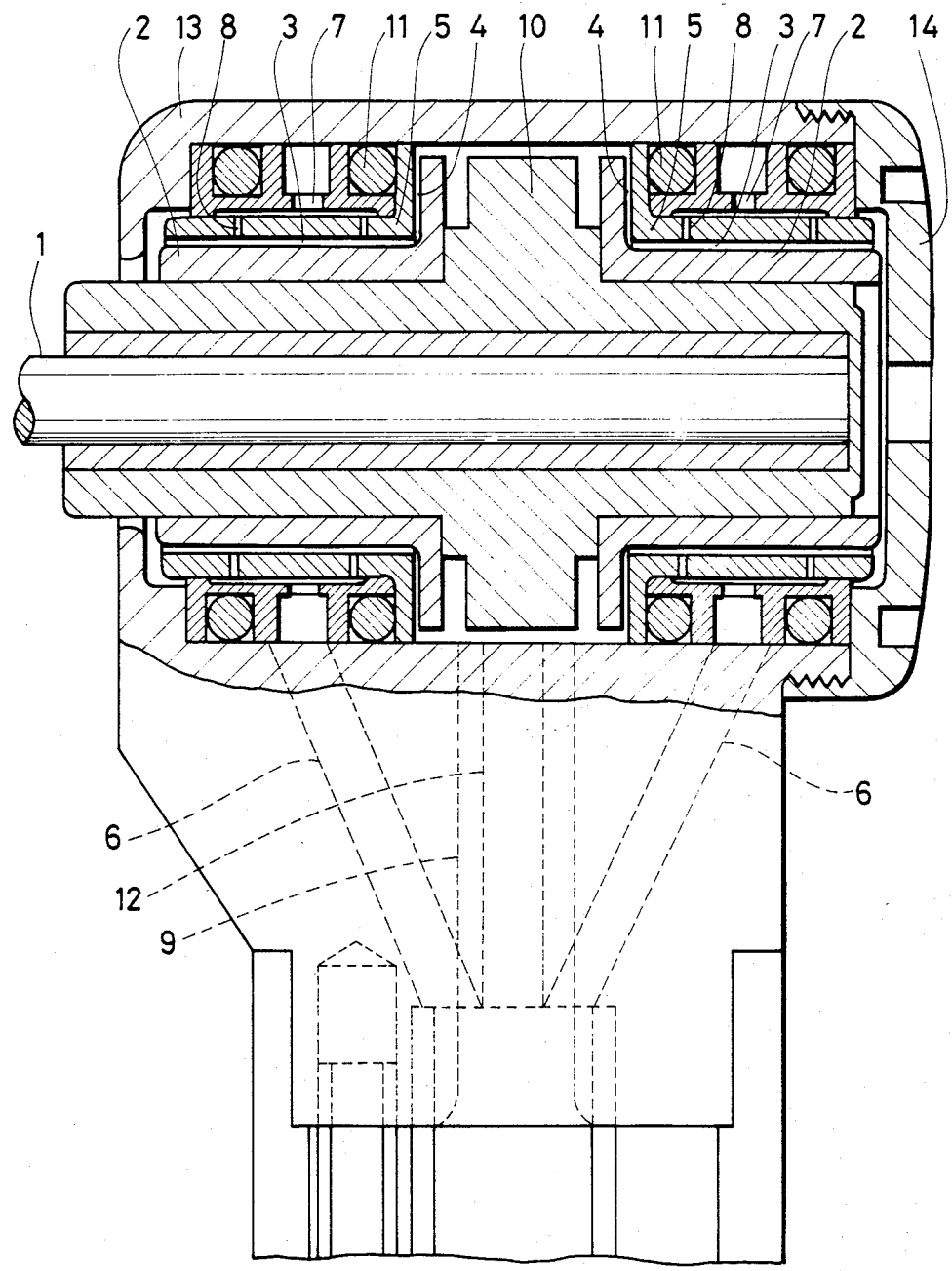
FIG. 1 is a front view in vertical section of a prior art dental handpiece.

The present invention relates to an air bearing device in dental handpiece of the type in which a turbine rotor 2 with a cutting tool shaft 1 set therethrough is journaled by an air bearing which is disposed with a radial gap 3 and a thrust gap 4 against the rotor 2. The radial gap 3 is provided with a plurality of partially enlarged gaps 31, which work as air pools, with respect to the longitudinal and peripheral directions of the bearing 5. The partially enlarged gaps 31 do not communicate with the longitudinal ends 32 and 33 of the radial gaps 3 nor to one another. The longitudinal length l of the enlarged gap 31 is larger than the peripheral width W thereof.

Figure 2:
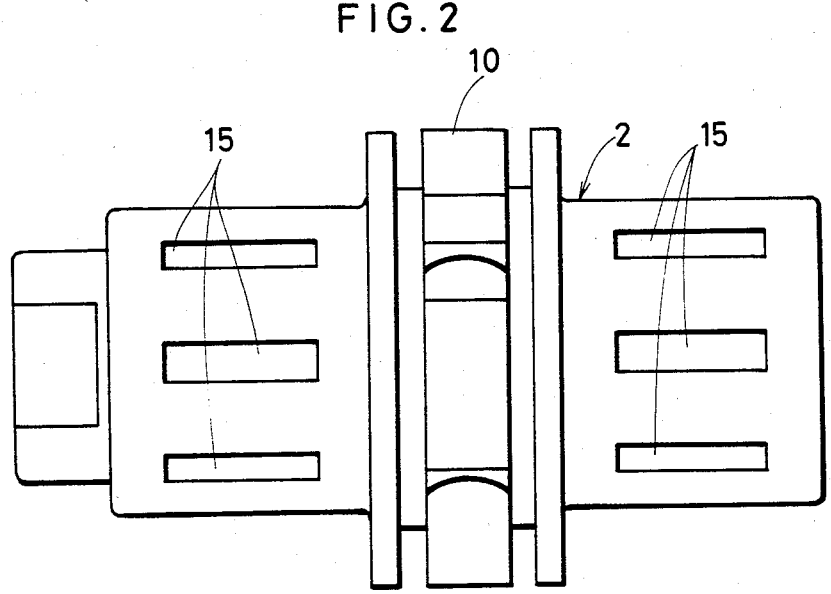
FIG. 2 is a side view of a rotor of the present invention.
Figure 5:
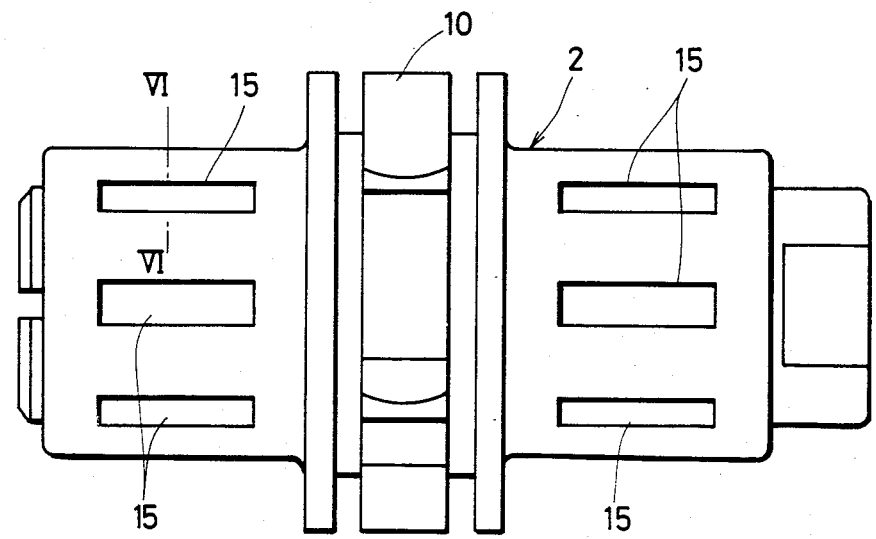
FIG. 5 is a side view of the rotor of another embodiment of the present invention.
Figure 6:
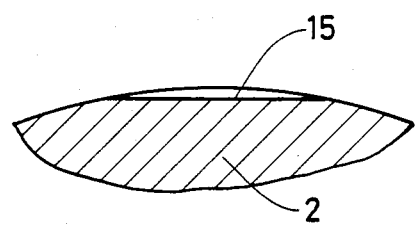
FIG. 6 is a sectional view taken along the line VI—VI of FIG. 5.

As the enlarged gaps 31 shown in FIG. 2 are a multiplicity of parallel longitudinally oblong recesses 15 which are spacedly provided in the periphery of the rotor 2, and the number of the gaps (or recesses) is 8 for each rotor 2 before or after the turbine blades 10. In another embodiment shown in FIGS. 5 and 6, oblong recesses 15 are provided which are also parallel with one another and, unlike in the aforesaid embodiment, are in slightly bow-sectioned shape, though either is acceptable.

It is also possible to form the recesses 15 on the inner face (opposite to the rotor surface) of the bearing 5 to attain substantially the same structure as that described above. It is not necessary that the recesses 15 be parallel with one another. The recesses 15 may be in any shape as long as they do not communicate with one another. Furthermore, the recesses 15 need not be uniform in depth, nor is there any limit to the number thereof.

It will be readily understood that such recesses 15 result in forming partially enlarged gaps 31 between the bearing 5 and the rotor 2 substantially larger longitudinally as well as peripherally than the unmodified radial gap 3. One thing common in the prior art of FIG. 1 and the present invention is that the air bearing is of the inherent throttling or orifice throttling type. In the air bearing of such throttling type, the inner pressure of the bearing varies dependent upon the size of the bearing gap from the moment when the supply of compressed air through orifices 8 is started to obtain the proper load capacity and/or bearing stiffness, and there are provided a plurality of orifices which do not communicate with one another in the bearing gap through grooves or the like. Of air bearings of the surface throttling type, on the other hand, there are those whose orifices communicate with one another or those with a single orifice having grooves to distribute the air throughout the bearing interior arranged over the entire periphery of the bearing body. These are apparently different from those of the inherent or surface throttling type. In the present invention, the air bearing is made to be of the inherent or orifice throttling type by providing the recesses 15 in the manner that they do not communicate with one another, especially, peripherally.

The function of the above-mentioned partially enlarged gap 31 will be explained.

Figure 3:
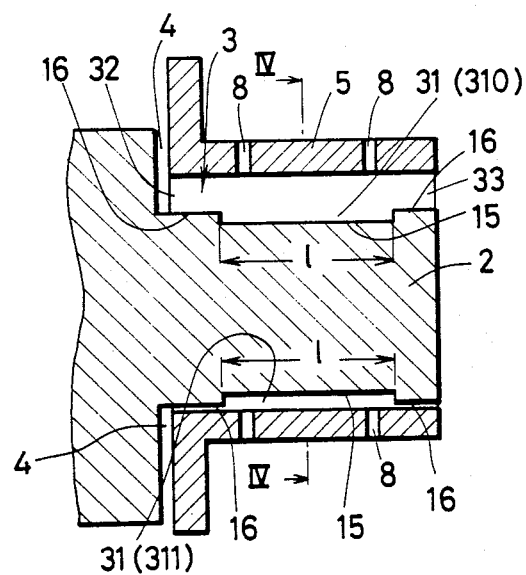
FIG. 3 is a sectional view showing an air bearing device according to the invention wherein the rotor of FIG. 2 housed in the bearing is off-centered.
Figure 4:
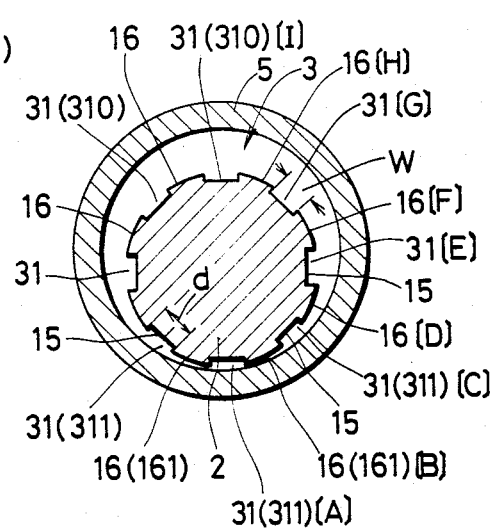
FIG. 4 is a sectional view taken along the line IV—IV of FIG. 3.

Referring to FIGS. 3 and 4, when the peripheral face of the rotor 2, other than the recesses or recessed parts 15, is taken as the raised parts 16 and the longitudinal flow of the air in FIG. 3 is considered, the air having entered through the orifices 8 comes into the partially enlarged gap 31; However, as seen in the upper partially enlarged gap 310 in FIG. 3, the gaps 31 are relatively broad even at both longitudinal open ends of the bearing 5; therefore, the air escapes easily to outside of the bearing 5 and the pressure in the gap cannot be maintained. Meanwhile, the lower gap 311 is fairly narrow at both longitudinal open ends due to the raised parts 10, so that the air in the gap 31 is not easily released longitudinally. Nor is it easily released peripherally because of the narrow gap between the raised part 16 and the inside face of the air bearing 5 (this gap being the narrowest over the lowermost raised parts 161). Thus a high pressure is maintained in the gaps 3 over one side of the rotor 2 toward which it is decentered. Therefore, a force required to keep the rotor 2 at the normal concentric position acts thereon increasing the bearing stiffness or load capacity. In the above case, the rotor 2 is off-centered at maximum, but the effect described earlier is obtained tendentiously regardless of the amount of eccentricity of the rotor. It may be readlly understood that one structural prerequisite for this effect is that the gaps 3 less easily communicate through both longitudinal ends 32 and 33 and peripherally with one another. Another prerequisite is that the longitudinal length l of the partially enlarged gap 31 be larger than the peripheral width W. If the relationship between such length and width is reversed, the peripheral air flow becomes greater than the longitudinal air flow. The effect of the present invention will be well exhibited. If the relationship l>W is maintained, the pressure in the space defined by the raised parts 161 of the rotor 2 and the bearing 5 in FIG. 4 decreases gradually even when the width of the partially enlarged gap 31 is small unlike an air bearing without recesses (in the rotor 2), resulting in almost the same bearing capacity. It is, therefore, not necessary to set any limit to peripheral width W.

Figure 7:
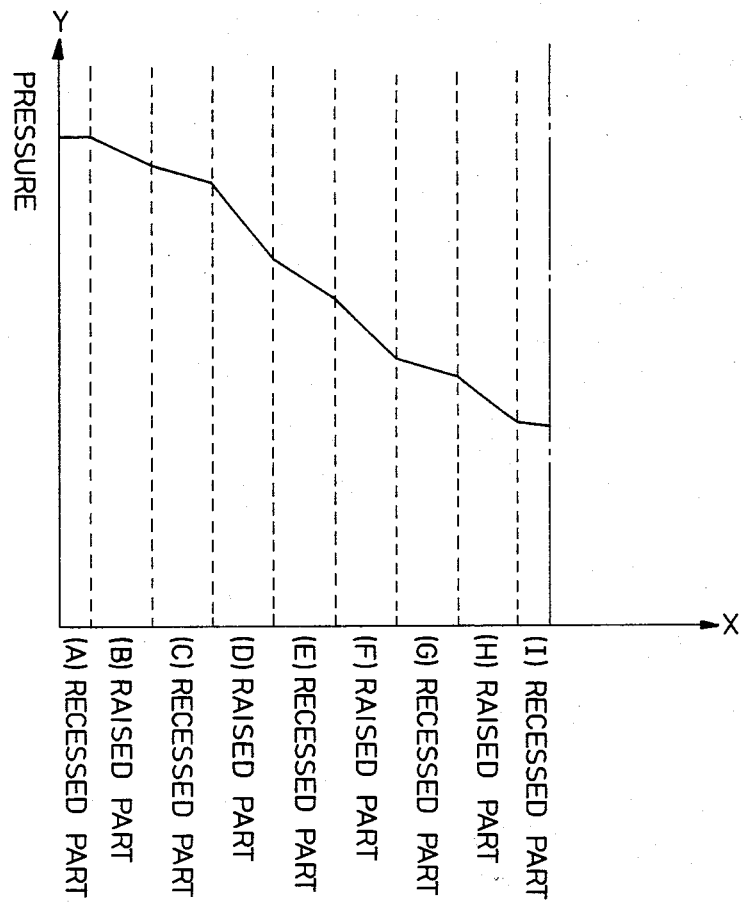
FIG. 7 is a pressure distribution curve for the handpiece of the present invention.

Referring now to FIG. 7 showing pressure distribution characteristics, given is a set of data demonstrating the effect of the present invention which is described below. In the graph, the partially enlarged gaps 31 represented by A, C, E, G and I in FIG. 4 and the raised parts 16 represented by B, D, F and H are plotted on the axis of abscissa, and the air pressure is plotted on the ordinate. The air pressures in the respective recesses and raised parts 31 and 16 when the air flows in the peripheral direction are shown as functions of the positions thereof. From the graph it is apparent that the peripheral distribution of the pressure is considerably high. Tests of the embodiments of FIGS. 2, 3 and 4 showed that the normal rotational speed could be maintained with an air pressure of 3.5 kgf/cm$^2$ even when the overall length of the cutting tool 1 is 25 mm and its weight is 600 mg. It is also found that when a test bar 1.6 mm in diameter and 20 mm in length is used, there is no contact between the bearing 5 and the rotor 2 even at an air pressure of 1.8 kgf/cm$^2$. With conventional handpieces (of air bearing type), the maximum overall length usable at an air pressure of 3.5 kgf/cm$^2$ maximum is 22 mm and the maximum weight usable is 400 mg. This means that according to the present invention up to 200 mg heavier and up to 3 mm longer cutting tool is usable.

As seen from the above, a handpiece according to the present invention has an appreciably higher bearing stiffness even at a low air pressure. This means that cutting is feasible even if the air pressure is lowered due to compressor trouble often encountered in a dental clinic; also, when the pressure is normal, a larger cutting tool can be used without sacrificing the cutting performance.

Although the increase in bearing stiffness mentioned above seems to suggest an increase in load capacity, described below as further substantiation is the results of a test in which measurement was taken on the load at which the rotor 2 started to come into contact with the bearing 5 with various loads applied to the cutting tool 1. While the contact started at a load of 100 g with a conventional counterpart, no contact was found in a handpiece of the present invention even when the load was increased to 120 g.

FIG. 8 shows the rotational speed and stability as a function of the air pressure when the handpiece is fitted with a test bar (1.6 mm in diameter, 20 mm long).

In the figure, the curve a shows the speed and pressure relationship of a prior art handpiece, and the curve b shows such relationship of a handpiece of the present invention. Mark "x" indicates unstable rotation at the particular speed, and mark "o" indicates stable rotation. The graph in FIG. 8 shows that the handpiece of the present invention can be operated at a higher rotational speed than the prior part counterpart at any air pressure in the acceptable range. Moreover, even under a high load with the air pressure ranging from 2.0 to 3.5 kgf/cm$^2$, high-speed operation is available with an excellent running stability for the handpiece of this invention. In contrast thereto, a prior art counterpart is only stable during running when the air pressure is 3.5 kgf/cm$^2$, and it runs unstably when the air pressure is lower than that.

In the embodiments shown above, the present invention is applied to handpieces each with a pair of bearings, but this invention is equally applicable also to those with one bearing for one rotor (that is, of the cantilever type).

Thus, the present invention has a number of outstanding effects and advantages, namely improved cutting performance of the handpiece, increased bearing stiffness as well as load capacity, reduced risk of abnormal running noise and vibration due to the whirl phenomenon, improved concentricity and durability and so on.

Having described our invention as related to the embodiment shown in the accompanying drawing, it is intended that the invention be not limited by any of the details of description, unless otherwise specified, but rather be constructed broadly within its spirit and scope as set out in the accompanying claims.

We claim:

1. An air bearing device in a dental handpiece of the type in which a turbine rotor having a cutting tool shaft set therethrough is journaled by a bearing disposed with a radial gap and a thrust gap between said rotor and said bearing wherein:

said radial gap being defined radially by peripheral walls comprising the inner peripheral wall of said bearing and the outer peripheral wall of said rotor, and being defined longitudinally by said radial gap at one end and by the end of said bearing at the other end;

said radial gap is provided with a plurality of partially enlarged longitudinal gaps in said peripheral walls serving as air pools;

each said partially enlarged gap being isolated from one another and from said ends; and the longitudinal length of said enlarged gap is larger than the peripheral width thereof.

2. An air joural device as recited in claim 1, wherein said partially enlarged gaps are essentially composed of a multiplicity of recesses which are oblong longitudinally to said bearing and spaced peripherally on said bearing.

3. An air journal device as recited in claim 1, wherein said partially enlarged gaps are essentially composed of a multiplicity of recesses which are oblong longitudinally to said bearing and spaced peripherally on said turbine rotor.

* * * * *